(12) United States Patent
Khandelwal et al.

(10) Patent No.: US 12,384,736 B2
(45) Date of Patent: Aug. 12, 2025

(54) PROCESS AND PLANT FOR PREPARING PURIFIED BENZENE COMPOSITION FROM CRUDE HYDROCARBON STREAM CONTAINING BENZENE

(71) Applicant: SULZER MANAGEMENT AG, Winterthur (CH)

(72) Inventors: Rahul Khandelwal, Katy, TX (US); Joseph C. Gentry, Houston, TX (US)

(73) Assignee: SULZER MANAGEMENT AG, Winterthur (CH)

( * ) Notice: Subject to any disclaimer, the term of this patent is extended or adjusted under 35 U.S.C. 154(b) by 114 days.

(21) Appl. No.: 18/021,545

(22) PCT Filed: Aug. 17, 2021

(86) PCT No.: PCT/EP2021/072812
§ 371 (c)(1),
(2) Date: Feb. 15, 2023

(87) PCT Pub. No.: WO2022/038123
PCT Pub. Date: Feb. 24, 2022

(65) Prior Publication Data
US 2023/0303467 A1 Sep. 28, 2023

Related U.S. Application Data

(60) Provisional application No. 63/068,212, filed on Aug. 20, 2020.

(30) Foreign Application Priority Data

Sep. 4, 2020 (EP) .................................... 20194570

(51) Int. Cl.
*C07C 7/08* (2006.01)
*B01D 3/14* (2006.01)
(Continued)

(52) U.S. Cl.
CPC .............. *C07C 7/005* (2013.01); *B01D 3/141* (2013.01); *B01D 3/143* (2013.01); *B01D 3/32* (2013.01);
(Continued)

(58) Field of Classification Search
None
See application file for complete search history.

(56) References Cited

U.S. PATENT DOCUMENTS 2,627,495 A   2/1953   Lanning
2,722,502 A * 11/1955 Lien ...................... C10G 17/07
                                                 208/263
(Continued)

FOREIGN PATENT DOCUMENTS

CN   101899325 A   12/2010
CN   106221794 A   12/2016
(Continued)

OTHER PUBLICATIONS

European Search Report issued Feb. 17, 2021 in corresponding European Application No. 20194570.6.
(Continued)

*Primary Examiner* — Tam M Nguyen
(74) *Attorney, Agent, or Firm* — Global IP Counselors, LLP (57) ABSTRACT

A process for preparing a purified benzene composition from a crude hydrocarbon stream containing at least 10% by volume of benzene is provided. The process comprises subjecting the crude hydrocarbon stream and a further recycled benzene containing stream to a solvent-based extraction so as to produce a benzene enriched aromatic stream and a benzene depleted non-aromatic stream, subjecting the benzene enriched aromatic stream to a hydrodesulfurization so as to obtain a desulfurized aromatic stream, (Continued)

subjecting the desulfurized aromatic stream to a distillation producing a purified benzene stream and a further benzene containing stream having a benzene concentration of between less than 100% by weight and the azeotropic benzene concentration, and at least partially recycling the further benzene containing stream.

11 Claims, 6 Drawing Sheets

(51) Int. Cl.
*B01D 3/32* (2006.01)
*B01D 3/40* (2006.01)
*B01D 11/04* (2006.01)
*C07C 7/00* (2006.01)
*C07C 7/10* (2006.01)
*C07C 7/17* (2006.01)

(52) U.S. Cl.
CPC ............ *B01D 3/40* (2013.01); *B01D 11/0492* (2013.01); *C07C 7/08* (2013.01); *C07C 7/10* (2013.01); *C07C 7/17* (2013.01)

(56) References Cited

U.S. PATENT DOCUMENTS

| | | | |
|---|---|---|---|
| 3,023,158 A | 2/1962 | Watkins | |
| 3,331,766 A | 7/1967 | Young | |
| 3,449,460 A * | 6/1969 | Tarhan | C10G 65/00 208/78 |
| 6,540,907 B1 * | 4/2003 | Towler | B01D 3/141 208/237 |
| 9,144,752 B2 | 9/2015 | Koseoglu | |
| 9,856,425 B2 | 1/2018 | Ward et al. | |
| 10,118,878 B2 | 11/2018 | Gattupalli et al. | |
| 10,513,664 B1 | 12/2019 | Koseoglu | |
| 11,339,336 B2 | 5/2022 | Koseoglu | |
| 2007/0000809 A1 * | 1/2007 | Lin | C10G 21/00 208/254 R |
| 2012/0067776 A1 | 3/2012 | Diehl et al. | |
| 2013/0062251 A1 | 3/2013 | Koseoglu | |
| 2016/0369190 A1 | 12/2016 | Ward et al. | |
| 2020/0190414 A1 | 6/2020 | Koseoglu | |
| 2020/0354293 A1 * | 11/2020 | Tsai | B01D 3/143 |
| 2021/0238137 A1 * | 8/2021 | Jo | C08G 75/0204 |
| 2024/0376027 A1 * | 11/2024 | Pacheco | C07C 7/04 |

FOREIGN PATENT DOCUMENTS

| | | |
|---|---|---|
| EA | 030559 B1 | 8/2018 |
| GB | 608605 A | 9/1948 |
| JP | H07-196542 A | 8/1995 |
| JP | 2009-084227 A | 4/2009 |
| JP | 2012-519716 A | 8/2012 |
| SU | 331535 A3 | 3/1972 |
| WO | 2013019592 A2 | 2/2013 |
| WO | 2019/105766 A1 | 6/2019 |
| WO | 2020131336 A1 | 6/2020 |

OTHER PUBLICATIONS

International Search Report and Written Opinion issued Nov. 16, 2021 in corresponding International Application No. PCT/EP2021/072812.

Written Opinion issued Aug. 22, 2022 in corresponding International Application No. PCT/EP2021/072812.

International Preliminary Report on Patentability issued Nov. 18, 2022 in corresponding International Application No. PCT/EP2021/072812.

Russian Office Action of corresponding Russian case dated Aug. 23, 2024.

Russian Search Report of corresponding Russian case dated Aug. 23, 2024.

First Office Action received in Chinese Application No. 202180071782.6, issued on Feb. 25, 2025, 41 pages. (English Translation Submitted).

* cited by examiner

PROCESS AND PLANT FOR PREPARING PURIFIED BENZENE COMPOSITION FROM CRUDE HYDROCARBON STREAM CONTAINING BENZENE

CROSS-REFERENCE TO RELATED APPLICATION

This application is a U.S. National Stage application of International Application No. PCT/EP2021/072812, filed Aug. 17, 2021, which claims priority to European Application No. 20194570.6, filed Sep. 4, 2020 and U.S. Provisional Application No. 63/068,212, filed Aug. 20, 2020, the contents of each of which are hereby incorporated by reference.

BACKGROUND

Field of the Invention

The present disclosure relates to a process and a plant for preparing a purified benzene composition from a crude hydrocarbon stream containing benzene.

Benzene is an important starting material for the synthesis of a plurality of chemical compounds, such as ethyl benzene, cumene, cyclohexene, nitrobenzene and others. These compounds, in turn, are starting materials for the synthesis of other compounds, such as styrene, phenol, acetone, cyclohexanol and aniline, which are important precursors of polymers, such as polystyrenes, styrene-butadiene-rubbers, polyamides and epoxy resins, of washing active substances, such as alkylbenzene sulfonic acids, of solvents, of pesticides, of colorants and of others. On account of this reason, benzene is in fact one of the most produced chemicals in the world.

Background of the Invention

There are several processes for benzene production known, such as catalytic reforming, steam cracking, hydrodealkylation (HAD) of toluene, toluene disproportionation (TDP), Coke Oven Light Oil (COLO) extraction, LPG Cyclar, Gas to Aromatics etc. However, the dominant production routes are steam cracking and catalytic reforming. In either of these production routes, a solvent based extraction unit is used for extracting petrochemical grade benzene from pyrolysis gasoline (also called pygas) coming from steam cracker or reformate stemming from catalytic reforming. There is an increasing trend among refiners to extract aromatics, like benzene from Fluid Catalytic Cracking (FCC) gasoline. This trend is attributed to the projected growth in petrochemicals as opposed to declining or stagnant refinery fuels demand. Traditionally, for gasoline benzene management, the benzene contained in FCC gasoline has been taken as a benzene heart cut from a naphtha splitter on FCC gasoline. The benzene rich cut is then sent to either a dedicated benzene saturation unit or light naphtha isomerization or catalytic reforming unit. There are two major drawbacks in either of these approaches. Firstly, the benzene rich heart cut has a significant quantity of high-octane olefins which get saturated when sent to the naphtha hydrotreater upstream of naphtha isomerization or catalytic reforming unit. Alternatively, if sent to a dedicated benzene saturation unit, also an octane loss occurs. This octane loss then needs to be compensated by the refinery octane producing units such as isomerization, reforming, alkylation etc. Further, the presence of benzene is an unwanted feature of light naphtha isomerization feed. Secondly, the value of benzene, as a petrochemical commodity, in routes likes isomerization or benzene saturation gets lost.

Hence, because of the above-mentioned drawbacks in existing benzene management approaches and the projected increasing trend of petrochemicals over refinery fuels, refiners are now interested in the option of extracting aromatics, like benzene, from FCC gasoline, while at the same time avoiding octane loss coming from the saturation of the high octane olefins. However, this is not simple and straightforward. FCC gasoline, as opposed to reformate or pygas, is a challenging feedstock for solvent extraction because of the high presence of naphthenes, cyclic olefins and olefins. These compounds, due to their polarity, close boiling points and azeotrope formation behavior, are difficult to separate from aromatics. The benzene rich or $C_6$-$C_8$-FCC naphtha cut, when fed into a solvent based extractive distillation configuration, results into the following streams: Firstly, an olefinic rich raffinate which can be sent directly to gasoline pool for blending since most of the sulfur has been extracted away, and secondly a benzene or aromatics (benzene, toluene and mixed xylenes) rich extract containing sulfur species.

SUMMARY

For extracted aromatics, like Benzene, to qualify for petrochemical grade specification, a total sulfur specification of less than 1 ppmw (parts per million by weight) and a total nitrogen specification of less than 1 ppmw is required. For aromatics, like toluene and mixed xylenes, the sulfur specification is relatively less stringent and is usually less than 10 ppmw depending on downstream application. As explained above, the extraction of aromatics from FCC gasoline results also in accompanying removal of sulfur species, like mercaptans, disulfides and thiophenes, in the order thiophenes>disulfides>mercaptans. A hydrodesulfurization (HDS) unit block is put downstream of extracted aromatics to meet the required sulfur and nitrogen specification. Some key design considerations of designing this HDS unit includes proper selection of catalyst and operating conditions like pressure and temperature in tandem with proper design of upstream extractive distillation unit and solvent's choice. This need stems from the following reasons. Firstly, aromatics saturation, like benzene getting saturated to cyclohexane (ring loss), needs to be minimized otherwise the purity of the downstream benzene product will be impacted irreversibly since there is no other method in the system to restore benzene purity. If higher than design value benzene ring loss, typically restricted to less than 0.1 wt % ring loss, is encountered in real life operations, then only re-extraction or solution by dilution with a large reformate or pygas extracted benzene pool or sending to downstream reformer unit are the available choices for the refiner. Either of these approaches represent an economic loss to the refiner since it implies additional capital and utility expenditure (in case of re-extraction) or impacting overall refinery benzene purity (in case of solution by dilution) or taking up additional capacity (in case of reformer routing) which could have been otherwise used for pushing more benzene production by pushing additional throughput of heavy naphtha reformer feedstock. Secondly, the HDS catalyst has an operating envelope starting from start-of-run (SOR) to end-of-run (EOR) which spans its cycle length. During SOR conditions, a ring loss can be below design value. However, as the catalyst ages, the inlet temperature to the reactor is increased to compensate for loss of catalyst activity. The increase in temperature can again trigger higher than design value ring loss leading to benzene purity getting affected. Thirdly, refiners nowadays are processing heavier and challenging feedstocks in their residue fluid catalytic cracking (RFCC) or fluid catalytic cracking (FCC) units. This can lead to higher than expected sulfur content at the inlet of the HDS reactor again triggering ring loss above design value. Fourthly, the olefin content is to be minimized at the inlet of the HDS reactor. This is largely accomplished by proper solvent selection and design of the upstream extraction unit. While meeting sulfur specifications such as less than 1 ppmw, olefin saturation across HDS occurs which leads to exotherm. The exotherm can again lead to higher than expected ring loss. Lastly, the presence of trace amount of $C_6$-cyclic olefins (such as cyclohexene or methylcyclopentene) in the extracted aromatics can again cause benzene purity concerns. The $C_6$-cyclic olefins are largely removed in the upstream extraction section. However, some slippage into extract can occur since these compounds are difficult to separate from aromatics in solvent based extractive distillation system. These cyclic olefins will undergo saturation to $C_6$-naphthenes (cyclohexane or methyl cyclopentane) across the HDS while meeting the required sulfur specification. Hence, benzene purity can be impacted because of slippage of C6 cyclic olefins into extract from upstream extractive distillation unit block.

In light of above, the object of the present disclosure is to provide a process and a plant for preparing a purified benzene composition from a crude hydrocarbon stream containing benzene (such as in particular a $C_6$-cut or $C_6$-$C_8$-cut of FCC gasoline or of COLO) comprising a solvent based extraction step and a hydrodesulfurization step, which reliably ensures a high purity benzene product even in the case of having higher than expected benzene ring loss during the hydrodesulfurization step because of the factors as explained above, wherein the high purity of the benzene is not even impacted in the case of a slippage of $C_6$-cyclic olefins or of $C_7$-iso-olefins from the upstream extraction section.

In accordance with the present disclosure this object is satisfied by providing a process for preparing a purified benzene composition from a crude hydrocarbon stream containing at least 10% by volume of benzene comprising the following steps:
a) subjecting the crude hydrocarbon stream and the further benzene containing stream recycled in step d) to a solvent based extraction so as to produce a benzene enriched aromatic stream and a benzene depleted non-aromatic stream,
b) subjecting the benzene enriched aromatic stream obtained in step a) to a hydrodesulfurization so as to obtain a desulfurized aromatic stream,
c) subjecting the desulfurized aromatic stream obtained in step b) to a distillation so as to produce a purified benzene stream and a further benzene containing stream having a benzene concentration of between less than 100% by weight and the azeotropic benzene concentration, and
d) at least partially recycling the further benzene containing stream obtained in step c) to step a).

The term "further benzene containing stream having a benzene concentration of between less than 100% by weight and the azeotropic benzene concentration" means in accordance with the present disclosure a stream, wherein the stream has a concentration of benzene of between less than 100% by weight and the final azeotropic benzene concentration as dictated by the vapor-liquid equilibrium of the compounds contained in the further benzene containing stream, wherein the further benzene containing stream comprises benzene and at least one of cyclohexane, methylcyclopentane, 2,3 dimethyl pentane and 2,4 dimethyl pentane. In other words, when the further benzene containing stream contains only benzene and cyclohexane, the azeotropic benzene concentration is the concentration of benzene in the azeotrope formed of these two components, i.e. the azeotrope of benzene and cyclohexane. If the further benzene containing stream contains benzene, cyclohexane and methylcyclopentane, then the azeotropic benzene concentration is the concentration of benzene in the azeotrope formed of these three components. i.e. the azeotrope of benzene, cyclohexane and methylcyclopentane. All subsequent references to "benzene and cyclohexane containing stream" in fact means further benzene containing stream having a benzene concentration of between less than 100% by weight and the azeotropic benzene concentration, wherein the further benzene containing stream comprises benzene and at least one of cyclohexane, methylcyclopentane, 2,3 dimethyl pentane and 2,4 dimethyl pentane. Thus, the further benzene containing stream is a benzene and at least one of cyclohexane, methylcyclopentane, 2,3 dimethyl pentane and 2,4 dimethyl pentane containing stream.

By performing the distillation in step c) so that the desulfurized aromatic stream obtained in the hydrodesulfurization of step b) is separated into a purified benzene stream and a further benzene containing stream comprising in addition to benzene at least one of cyclohexane, methylcyclopentane, 2,3 dimethyl pentane and 2,4 dimethyl pentane with the above mentioned benzene concentration and by recycling the further benzene containing stream at least partially and preferably completely to the solvent based extraction of step a), none or, if at all, only very minor amounts of the benzene contained in the further benzene containing stream is lost. More specifically, if at all, a negligible amount of benzene contained in the further benzene containing stream can be lost during the solvent based extraction into the raffinate (or benzene depleted non-aromatic stream, respectively), while virtually all of the benzene is extracted by the solvent into the benzene enriched aromatic stream. By subjecting the benzene enriched aromatic stream after the solvent based extraction to a hydrodesulfurization so as to obtain a desulfurized aromatic stream and then subjecting it to the distillation, the purity of the final benzene product stays unaltered even if higher than expected ring loss (of for instance 0.4 wt % real life operations versus 0.1 wt % design value) is encountered during the hydrodesulfurization step. Additionally, even if there should be a slippage of $C_6$-cyclic olefins and/or $C_7$-iso-olefins from the solvent based extraction step into the benzene enriched aromatic stream, then these compounds are also reliably separated from the benzene, since the saturated form of these compounds (i.e. $C_6$-naphthenes or $C_7$-iso-paraffins), as they are formed during the hydrodesulfurization step, form azeotropes with benzene too. Another important feature of the process of the present disclosure is that it is not required to produce in the distillation of step c) a further benzene and at least one of cyclohexane, methylcyclopentane, 2,3 dimethyl pentane and 2,4 dimethyl pentane containing stream with the final azeotropic composition. Instead, only a further benzene and at least one of cyclohexane, methylcyclopentane, 2.3 dimethyl pentane and 2,4 dimethyl pentane containing stream tending concerning its benzene concentration towards the azeotrope composition suffices for the purpose. In other words, in case of higher ring loss of 0.4 wt %, the distillation setup, downstream of the hydrodesulfurization can be designed to produce a further benzene containing stream with a benzene concentration of about 95 wt % instead of 52 wt % (which is the benzene concentration in the azeotrope of benzene and cyclohexane), which represents approximately 5% of the overall benzene quantity in the stream coming from downstream of hydrodesulfurization step. Thus, the impact of the recycle of the further benzene containing stream to the overall plant's capital and utility expenditure is minimal, wherein plant denotes herein the combination of the solvent based extraction unit the hydrodesulfurization unit and the (azeotropic) distillation unit. In particular, these advantageous effects are obtained, when a $C_6$-cut or $C_6$-$C_8$-cut of FCC gasoline or of COLO is used as feedstock of the process. In addition, these advantageous effects are obtained even in the case of a very long operation time including start-of-run to end-of-run operating temperature envelope of catalyst, in the case of heavier than expected feedstock being fed to the FCC, RFCC or COLO or in the case of slippage of $C_6$-cyclic olefins and/or $C_7$-iso-olefins into the benzene enriched aromatic stream obtained in the solvent based extraction step. More specifically, the obtained purified benzene stream has typically a benzene purity in excess of 99.8% and a content of sulfur containing compounds and of nitrogen containing compounds of less than 1 ppmw. The benzene product obtained qualifies for petrochemical grade and requires no further processing, such as re-extraction or dilution with a large pygas or reformate benzene pool.

As set out above, in step c) the desulfurized aromatic stream obtained in step b) is subjected to a distillation so as to produce a purified benzene stream and a further benzene containing stream having a benzene concentration of between less than 100% by weight and the azeotropic benzene concentration. Preferably, the distillation in step b) is performed so as to produce a purified benzene stream and a further benzene containing stream having a benzene concentration of between less than 99% by weight, more preferably less than 98% by weight, more preferably less than 97% by weight and even more preferably less than 96% by weight and the azeotropic benzene concentration, such as for instance a benzene concentration of 90 to 96% by weight. Alternatively preferred is that distillation in step b) is performed so as to produce a purified benzene stream and a further benzene containing stream having a benzene concentration of less than 90% by weight, more preferably of less than 80% by weight and more preferably of at most 70% by weight, such as for instance a benzene concentration of 70 to 90% by weight.

As set out above, a particular advantage of the present disclosure is that the process for preparing a purified benzene composition from a crude hydrocarbon stream containing at least 10% by volume of benzene is in particular suitable for processing a crude hydrocarbon stream having a comparable low benzene content, such as FCC or RFCC naphtha or COLO, in particular either from a $C_6$-cut or from a $C_6$-$C_8$-cut thereof. However, good results are also obtained when the crude hydrocarbon stream contains higher amounts of benzene, such as preferably, based on 100% by weight, at least 20% by volume, more preferably at least 30% by volume and even more preferably at least 50% by volume of benzene.

For instance, the process in accordance with the present disclosure allows to obtain highly purified benzene with a high yield from a crude hydrocarbon stream, which contains in addition to aromatics, based on 100% by weight, i) 20 to 60% by volume and preferably 30 to 50% by volume of paraffins, ii) 10 to 50% by volume and preferably 20 to 30% by volume of olefins and iii) 5 to 40% by volume and preferably 10 to 25% by volume of naphthenes.

Particular good results are obtained, when the crude hydrocarbon stream fed into the process in accordance with the present disclosure is a $C_6$-cut or a $C_6$-$C_8$-cut from fluid catalytic cracked naphtha or a $C_6$-cut or a $C_6$-$C_8$-cut from a coke oven light oil In accordance with the present disclosure, the crude hydrocarbon stream and the further benzene containing stream recycled in step d) are subjected to a solvent based extraction so as to produce a benzene enriched aromatic stream and a benzene depleted non-aromatic stream. This means in accordance with the present disclosure that the crude hydrocarbon stream and the further benzene containing stream recycled in step d) are separately from each other fed to the solvent based extraction unit, such as a solvent based extraction distillation unit, or the crude hydrocarbon stream and the further benzene containing stream recycled in step d) are mixed with each other to a combined feed stream, before being fed to the solvent based extraction unit, in which the solvent based extraction is performed.

Thus, in accordance with a particular preferred embodiment of the present disclosure, in step a) the crude hydrocarbon stream is mixed with the further benzene containing stream recycled in step d) to obtain a feed stream, which is subjected to the solvent based extraction. The crude hydrocarbon stream can be mixed with the recycled further benzene containing stream by using a mixer, such as a static mixer and/or a dynamic mixer, or merely by combining a line with the crude hydrocarbon stream and a line with the recycled further benzene containing stream to one line without any particular mixing device.

In accordance with an alternative embodiment of the present disclosure, the crude hydrocarbon stream and the further benzene containing stream recycled in step d) are separately from each other fed to the solvent based extraction unit, such as to an extractive distillation column. For instance, the hydrocarbon stream can be fed in the lower end of the extractive distillation column, whereas the further benzene containing stream recycled in step d) is fed to the extractive distillation column above thereof, or vice versa.

The present disclosure is not particularly limited concerning the kind of solvent based extraction performed in step a). Thus, in principle the solvent based extraction can be performed in an extraction column using no packing or using a packing, such as a structured packing and/or a random packing, or using trays for optimizing the contact area between the solvent on the one hand and the crude hydrocarbon stream and recycled further benzene containing stream on the other hand. Preferably, the solvent based extraction is performed in an extraction column, which contains trays.

Good results are in particular obtained, when the crude hydrocarbon stream and the further benzene containing stream recycled in step d) are subjected in step a) to an extractive distillation. In the extractive distillation, at the overhead of the distillation column the benzene depleted non-aromatic stream is obtained, whereas a stream comprising the aromatics and the solvent is obtained at the bottom of the distillation column. The stream comprising the aromatics and the solvent can then be led into a second distillation column, in which the aromatics (mainly benzene, if a $C_6$-cut is used, or a mixture of benzene, toluene and mixed xylenes, if a $C_6$-$C_8$-cut is used along with the sulfur species contained in the hydrocarbon feed stream) are separated from the solvent so that the solvent is obtained at the bottom of the second distillation column, which is usually called solvent recovery column, whereas the benzene enriched aromatic stream is obtained at the overhead of the distillation column. The solvent recovery column contains preferably in a part thereof a packing and in another part thereof trays.

In order to separate in step a) during the solvent based extraction the aromatics completely from the non-aromatics, it is proposed in a further development of the idea of the present disclosure to use in step a) a solvent having a comparably high polarity and a comparably high boiling point. Such solvents allow to excellently separate benzene and other aromatics in the solvent based extraction from the non-aromatics, because it has a high solubility for benzene and other aromatics, but displays a high rejection behavior for species, like cyclohexane (which can come from ring loss or cyclohexene slippage from the solvent based extraction and the saturation during the hydrodesulfurization), methylcyclopentane (which can come from methylcyclopentene slippage from the solvent based extraction and the saturation during the hydrodesulfurization) and 2,3 dimethyl pentane and 2,4 dimethyl pentane (which can come from $C_7$-iso-olefins slippage from the solvent based extraction and the saturation during the hydrodesulfurization). Moreover, it is of advantage that the solvent displays a high olefins (including cyclic olefins) rejection behavior so that the inlet of the downstream of hydrodesulfurization reactor has minimal olefin content. This is advantageous, because the presence of olefins in the hydrodesulfurization reactor can lead to exotherm due to saturation. The exotherm can trigger higher than design benzene ring loss.

Good results are in particular obtained, when the solvent used in step a) is selected from the group consisting of sulfolane, 3-methylsulfolane, 2,4-dimethylsulfolane, 3-ethylsulfolane, N-methyl pyrrolidone, 2-pyrrolidone. N-ethyl pyrrolidone, N-propyl pyrrolidone, N-formyl morpholine, dimethylsulfone, diethylsulfone, methylethylsulfone, dipropylsulfone, dibutylsulfone, tetraethylene glycol, triethylene glycol, dimethylene glycol, ethylene glycol, ethylene carbonate, propylene carbonate and arbitrary combinations of two or more thereof.

In accordance with a further particular preferred embodiment of the present disclosure, the solvent used in step a) comprises sulfolane combined with 3-methylsulfolane, N-formyl morpholine, 2-pyrrolidone, dipropylsulfone, tetraethylene glycol, water, heavy sulfur residuals from FCC gasoline or mixtures thereof as a co-solvent.

The present disclosure is not particularly limited concerning the type of hydrodesulfurization performed in step b) of the process in accordance with the present disclosure. Thus, the hydrodesulfurization can be performed as known and usual in the prior art. Good results are in particular obtained, when the benzene enriched aromatic stream is subjected in step b) together with hydrogen to a catalyst selected from the group consisting of alloys and compounds containing cobalt and molybdenum or containing nickel and molybdenum at a temperature of 200 to 500° C. More preferably, the temperature is 245° C. (SOR) to 300° C. (EOR) and the pressure during the hydrodesulfurization is 25 bara, wherein the hydrogen partial pressure is preferably in a range of 5 to 7 bara. The hydrodesulfurization unit preferably also removes the nitrogen species contained in the benzene enriched aromatic stream so as to ensure that the produced desulfurized aromatic stream fulfils the total nitrogen specification.

In a further development of the idea of the present disclosure it is suggested that the desulfurized aromatic stream is subjected in step c) to one or more distillation steps, wherein at least one distillation step is performed with a distillation column having 5 to 100 theoretical stages. However, it is more preferred that the desulfurized aromatic stream is subjected in step c) to at least one distillation step having more theoretical stages than usual in the prior art, in order to reliably separate in step c) the desulfurized aromatic stream into a purified benzene stream and a further benzene containing stream. Good results are in particular obtained, when the desulfurized aromatic stream is subjected in step c) to one or more distillation steps, wherein at least one distillation step is performed with a distillation column having 5 to 100 and preferably 10 to 80 theoretical stages. Best results are obtained, when in step c) at least one distillation step is performed with a distillation column having 15 to 60, more preferably 20 to 60 and most preferably 30 to 60 theoretical stages.

Usually, the distillation column has a reboiler at its bottom portion and a condenser at its overhead portion. If a top divided wall column is used, at the overhead portion two condensers can be provided, one at each side of the overhead portion.

As set out above, the desulfurized aromatic stream is separated in step c) into a purified benzene stream and a further benzene containing stream. Depending on the composition of the crude hydrocarbon stream, in addition to benzene only one of cyclohexane, methylcyclopentane, 2,3 dimethyl pentane and 2,4 dimethyl pentane, or two of cyclohexane, methylcyclopentane, 2,3 dimethyl pentane and 2,4 dimethyl pentane, or three of cyclohexane, methylcyclopentane, 2,3 dimethyl pentane and 2,4 dimethyl pentane or all of cyclohexane, methylcyclopentane, 2,3 dimethyl pentane and 2,4 dimethyl pentane can be contained in the further benzene containing stream.

Preferably, the distillation in step c) is performed at a pressure of 0.01 to 1.0 MPa, more preferably of 0.05 to 0.5 MPa, still more preferably of 0.13 to 0.17 MPa and most preferably of 0.10 to 0.20 MPa, such as about 0.15 MPa.

Moreover, it is preferred that the distillation in step c) is performed at a temperature of 80 to 180° C., more preferably of 90 to 160° C., still more preferably of 90 to 140° C. and most preferably 90 to 100° C.

In accordance with a further particular preferred embodiment of the present disclosure, the desulfurized aromatic stream is subjected in step c) to one or more distillation steps, wherein at least one distillation step is performed with a divided wall column, i.e. a column, in which a wall extends perpendicular to the vertical direction. Particular good results are obtained, when at least one distillation step is performed with a top divided wall column. Compared to a conventional 3 cut column for achieving the same overall result across the plant, a top divided wall column offers the advantage of reduced height and less energy consumption for the same number of total theoretical stages. It is to be noted that while making the comparison in terms of total number of theoretical stages, stages on either side of the wall need to be counted along with the stages below the wall. This embodiment is in particular preferable, when using as a crude hydrocarbon stream a $C_6$-cut or $C_6$-$C_8$-cut from fluid catalytic cracked naphtha or a $C_6$-cut or $C_6$-$C_8$-cut from a coke oven light oil.

According to a first variant of this embodiment, in step c) one distillation step is performed and the wall of the top divided wall column extends from the upper end of the top divided wall column downwards over 20 to 70% and preferably over 20 to 50% of the height of the top divided wall column. In this embodiment, at the left side of the overhead of the divided wall column an off-gas stream containing low molecular weight hydrocarbons, such as hydrogen, hydrogen sulfide, methane, ethane, propane and butane, is obtained, whereas at the right side of the overhead of the divided wall column the further benzene containing stream is obtained and at the bottom of the divided wall column the purified benzene stream is obtained. This embodiment is in particular suitable, when using as a crude hydrocarbon stream a $C_6$-cut from fluid catalytic cracked naphtha or stream a $C_6$-cut from a coke oven light oil.

This first variant is also in particular suitable, when using as a crude hydrocarbon stream a $C_6$-$C_8$-cut from fluid catalytic cracked naphtha or a $C_6$-$C_8$-cut from a coke oven light oil. In this case, at the bottom of the divided wall distillation column not a purified benzene stream (i.e. not a $C_6$-stream) is obtained, but a purified $C_6$-$C_8$-aromatics stream. This $C_6$-$C_8$-aromatics stream can then be easily processed, for instance in a conventional distillation column, so as to separate the $C_6$-$C_8$-aromatics stream into a purified benzene stream and one or more other aromatics streams.

In accordance with an alternative embodiment of the present disclosure, which is in particular suitable, when using as a crude hydrocarbon stream a $C_6$-$C_8$-cut from fluid catalytic cracked naphtha or a coke oven light oil, the desulfurized aromatic stream obtained in step b) is subjected in step c) to two distillation steps. It is preferred in this embodiment that the desulfurized aromatic stream obtained in step b) is subjected to a first distillation step in a first distillation column so as to obtain at the overhead of the first distillation column an offgas stream containing low molecular weight hydrocarbons, i.e. hydrogen, hydrogen sulfide, $C_1$-$C_4$-hydrocarbons, such as methane, ethane, propane and butane, whereas at the bottom of the first distillation column a liquid with the remaining compounds stream is obtained. Preferably, this liquid stream is subjected to a second distillation step in a second distillation column so as to obtain as side stream of the second distillation column the purified benzene stream, at the overhead of the second distillation column the further benzene containing stream and at the bottom of the second distillation column a $C_{7+}$-stream.

In a further preferred embodiment of the present disclosure, the desulfurized aromatic stream is subjected in step c) to two distillation steps, wherein the desulfurized aromatic stream is subjected to a first distillation step in a first distillation column so as to obtain at the overhead of the distillation column an off-gas stream containing low molecular weight hydrocarbons, such as hydrogen, hydrogen sulfide, methane, ethane, propane and butane, whereas at the bottom of the first distillation column a liquid with the remaining compounds stream is obtained. Preferably, this liquid stream is subjected to a second distillation step in a second divided wall column so as to obtain as a first side stream of the second distillation column the purified benzene stream, as a second side stream of the second distillation column a toluene rich stream, at the overhead of the second distillation column the further benzene containing stream and at the bottom of the second distillation column a stream enriched in xylenes. Preferably, the second divided wall column is a middle divided wall column, which is a column in which a wall extending perpendicular to the vertical direction. Preferably, the wall extends, seen from the bottom to the overhead of the second distillation column, from a point being located at 10 to 30% of the distance from the bottom to the overhead of the second distillation column to a point being located at 70 to 90% of the distance from the bottom to the overhead of the second distillation column.

Preferably, the ratio of the further benzene containing stream to the purified benzene stream obtained in step c) is 1 to 50% by volume, preferably 2 to 30% by volume, more preferably 2 to 20% by volume, even more preferably 3 to 10% by volume and most preferably 5 to 10% by volume.

In accordance with the present disclosure, in step d) the further benzene containing stream obtained in step c) is at least partially recycled to step a), i.e. the solvent based extraction. More preferably, in step d) at least 50% by volume, even more preferably at least 80% by volume, still more preferably at least 90% by volume and most preferably all of the further benzene containing stream obtained in step c) are/is recycled to step a), i.e. the solvent based extraction.

Another aspect of the present disclosure relates to a plant for purifying a crude hydrocarbon stream containing at least 10% by volume of benzene comprising:
  i) a solvent based extraction unit having at least one inlet line and an outlet line for a benzene enriched aromatic stream,
  ii) a hydrodesulfurization unit having an inlet line being connected with the outlet line of the solvent based extraction unit, and having an outlet line for a desulfurized aromatic stream,
  iii) a distillation unit having an inlet line being connected with the outlet line of the hydrodesulfurization unit, an outlet line for a purified benzene stream and an outlet line for a further benzene containing stream, and
  iv) a recirculation line connecting the outlet line for the further benzene containing stream of the distillation unit with one of the at least one inlet line of the solvent based extraction unit.

Preferably, the plant further comprises a mixing unit for mixing the crude hydrocarbon stream with the further benzene containing stream recycled via the recirculation line, wherein the mixing unit has an inlet line for the crude hydrocarbon stream, an inlet line for the further benzene containing stream and an outlet line for a mixture of the crude hydrocarbon stream and the further benzene containing stream, which is also called herein as feed stream.

In a further development of the idea of the present disclosure, it is proposed that the distillation unit comprises only one distillation column having 5 to 100, preferably 10 to 80, more preferably 15 to 60, still more preferably 20 to 60 and most preferably 30 to 60 theoretical stages.

In accordance with a further preferred embodiment of the present disclosure, it is preferred that the distillation column of the plant is a top divided wall column.

Good results are in particular obtained, w % ben the wall of the top divided wall column extends from the upper end of the top divided wall column perpendicular downwards over 20 to 70% and preferably over 20 to 50% of the height of the top divided wall column, which is the distance from the bottom to the overhead of the distillation column.

In an alternative embodiment of the present disclosure, it is preferred that the distillation unit comprises two distillation columns, wherein one of the two distillation columns has 5 to 100, preferably 10 to 80, more preferably 15 to 60, still more preferably 20 to 60 and most preferably 30 to 60 theoretical stages.

Preferably, the first of the two distillation columns has an inlet line being connected with the outlet line of the hydrodesulfurization unit, has 5 to 30 and preferably 15 to 20 theoretical stages and has at its bottom an outlet line for a liquid stream, wherein the second of the two distillation columns has an inlet line being connected with the outlet line for a liquid stream of the first distillation column, has the outlet line for a purified benzene stream and has the outlet line for a further benzene containing stream.

It is particularly preferred that the second distillation column is a middle divided wall column. Good results are in particular obtained, when the wall of the middle divided wall column extends, seen from the bottom to the overhead of the second distillation column, from a point being located at 10 to 30% of the distance from the bottom to the overhead of the second distillation column to a point being located at 70 to 90% of the distance from the bottom to the overhead of the second distillation column.

BRIEF DESCRIPTION OF THE DRAWINGS

Specific embodiments in accordance with the present disclosure are subsequently described with reference to the appended drawings and by examples.

FIG. 1b illustrates a more detailed schematic view of the solvent based extraction unit being part of the plant shown in FIG. 1a.

DETAILED DESCRIPTION

Figure 1A:
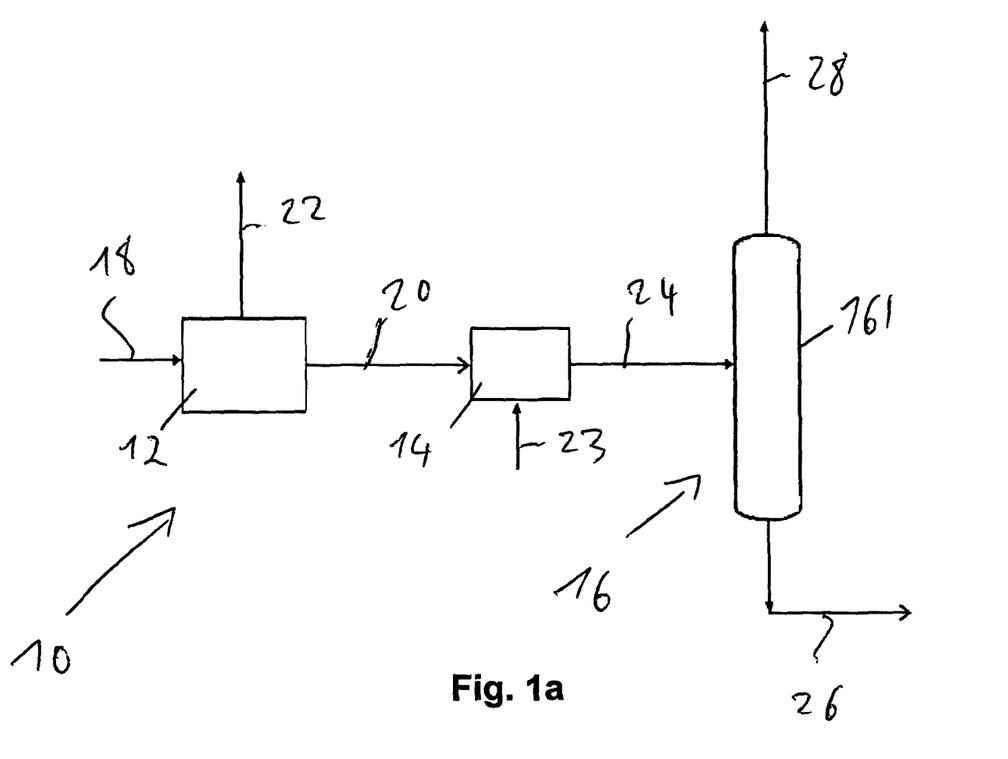
FIG. 1a illustrates a schematic view of a plant for preparing a purified benzene composition from a crude hydrocarbon stream containing benzene in accordance with the prior art.
Figure 1B:
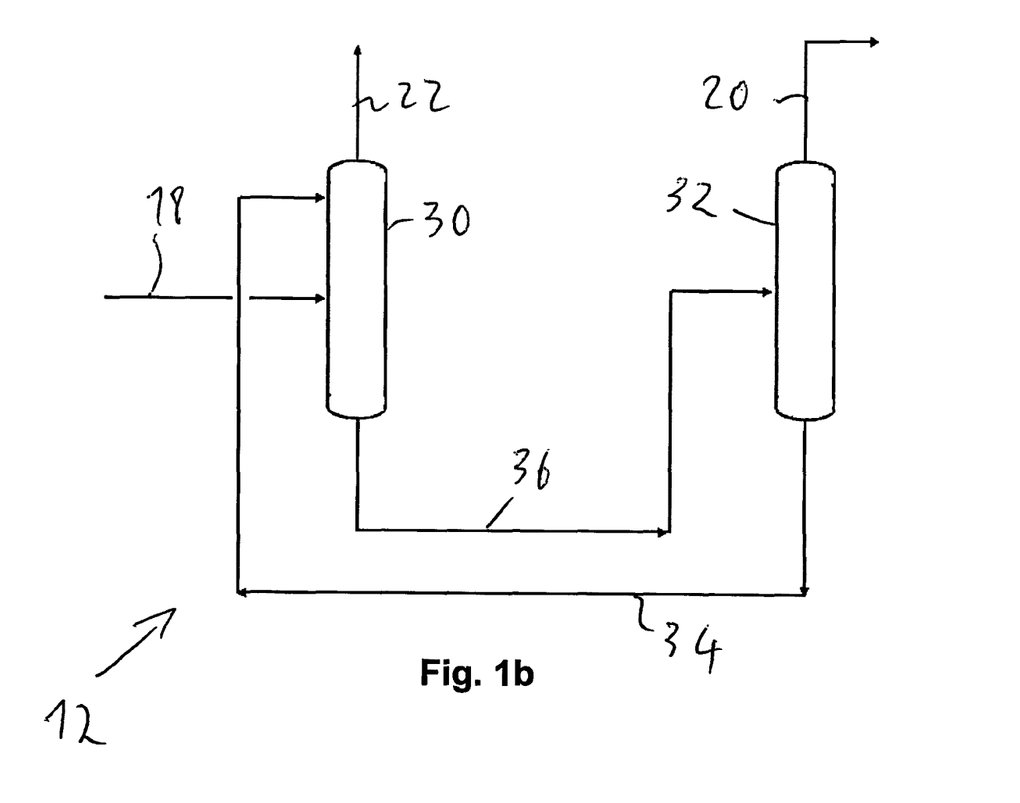

The plant 10 according to the prior art shown in FIGS. 1a and 1b comprises a solvent based extraction unit 12, a hydrodesulfurization unit 14 and a distillation unit 16. The solvent based extraction unit 12 comprises an inlet line 18 for feeding crude hydrocarbon stream into the solvent based extraction unit 12, an outlet line 20 for a benzene enriched aromatic stream and an outlet line 22 for a benzene depleted non-aromatic stream. The outlet line 20 for a benzene enriched aromatic stream is also the inlet line for the hydrodesulfurization unit 14, which further has an inlet line 23 for hydrogen as well as an outlet line 24 for desulfurized aromatic stream. The outlet line 24 for desulfurized aromatic stream is the inlet line for the distillation unit 16, which further has an outlet line 26 for purified benzene stream and an outlet line 28 for off-gas. The distillation unit 16 comprises one distillation column 16', which has 16 theoretical stages.

The solvent based extraction unit 12 is in more detail shown in FIG. 1b and comprises a first distillation column 30 and a second distillation column 32. The inlet line 18 for feeding crude hydrocarbon stream is connected with the middle part of the first distillation column 30. Moreover, a solvent (recirculation) line 34 leads into the upper part of the first distillation column 30. During the distillation, a benzene depleted non-aromatic stream is produced as overhead stream and is withdrawn from the first distillation column 30 via the outlet line 22. At the bottom of the first distillation column 30 a mixture of solvent and a benzene enriched aromatic stream is obtained, which is withdrawn from the first distillation column 30 via the line 36 and then fed into the second distillation column 32, in which the solvent is separated from the benzene enriched aromatic stream. While the regenerated solvent is led back from the bottom of the second distillation column 32 via the solvent (recirculation) line 34 into the upper part of the first distillation column 30, the benzene enriched aromatic stream is withdrawn from the overhead of the second distillation column 32 via line 20 and is fed into the hydrodesulfurization unit 14.

During the operation of the plant 10, the benzene enriched aromatic stream is fed via line 20 and hydrogen is fed via inlet line 23 into the hydrodesulfurization unit 14, in which the sulfur containing compounds as impurities are desulfurized into non-sulfur compounds and hydrogen sulfide. The hydrodesulfurization unit also removes the nitrogen species contained in the benzene enriched aromatic stream so as to ensure that the produced desulfurized aromatic stream fulfils the total nitrogen specification. The produced desulfurized aromatic stream is fed via line 24 into the distillation column 16'. An off-gas stream obtained during the distillation as overhead product and containing low molecular weight hydrocarbons, such as C1-C5-hydrocarbons, in particular methane, ethane, propane, butane, hydrogen (remained after the hydrodesulfurization) and hydrogen sulfide (produced during the hydrodesulfurization), is withdrawn from the distillation column 16' via outlet line 28, whereas the purified benzene stream obtained as bottom product is withdrawn from the distillation column 16' via outlet line 26.

In contrast thereto, the process performed in the plant 10 in accordance with the present disclosure shown in FIGS. 2 to 5 comprises the step of subjecting the desulfurized aromatic stream obtained in the hydrodesulfurization unit 14 to a distillation so as to produce a purified benzene stream and a further benzene containing stream, and the step of at least partially and preferably completely recycling the so obtained further benzene containing stream into the solvent based extraction unit 12. For this purpose, the plant 10 in accordance with the present disclosure shown in FIGS. 2 to 5 comprises a recirculation line 38 for the further benzene containing stream obtained in the distillation unit 16, wherein the recirculation line 34 connects the distillation unit 16 and the solvent based extraction unit 12. Moreover, the distillation unit 16 comprises for this purpose at least one distillation column having a suitable high number of theoretical stages so that the desulfurized aromatic stream obtained in the hydrodesulfurization unit 14 is separated during the distillation into a purified benzene stream and a further benzene containing stream. Preferably, the number of theoretical stages of this distillation column is 5 to 100, more preferably 10 to 80, even more preferably 15 to 60, still more preferably 20 to 60 and most preferably 30 to 60.

By performing the distillation in step c) so that the desulfurized aromatic stream obtained in the hydrodesulfurization of step b) is separated into a purified benzene stream and a further benzene containing stream, the at least one of cyclohexane, methylcyclopentane, 2,3 dimethyl pentane and 2,4 dimethyl pentane contained as impurities in the further benzene containing stream, is reliably and nearly completely separated from the purified benzene stream, thus leading to a benzene stream having a very high purity of for instance at least 99.8% by volume. Since the further benzene containing stream is recycled at least partially and preferably completely to the solvent based extraction of step a), none or, if at all, only very minor amounts of the benzene contained in the further benzene containing stream is lost. This is due to the fact that the further benzene containing stream is broken in the solvent based extraction step a) to a benzene enriched aromatic stream and a benzene depleted nonaromatic stream, i.e. the benzene and other aromatics contained in the further benzene containing stream are separated from the at least one of cyclohexane, methylcyclopentane, 2,3 dimethyl pentane and 2,4 dimethyl pentane contained as impurities or other impurities in form of olefins, paraffins, naphthenes and other non-aromatic compounds. By subjecting the benzene enriched aromatic stream after the solvent based extraction to a hydrodesulfurization so as to obtain a desulfurized aromatic stream and then by subjecting the desulfurized aromatic stream to a distillation so as to produce a purified benzene stream and a further benzene containing stream, the benzene recycled via the further benzene containing stream from the distillation to the solvent based extraction is indeed recovered. All in all, the process in accordance with the present disclosure allows to prepare from a crude hydrocarbon stream containing benzene reliably and with high yield a purified benzene composition with a high benzene concentration of for instance at least 99.8% by volume and the desired at most minimal amount of sulfur compound impurities of for example at most 1 ppmw, qualified as total sulfur, and total nitrogen content of less than 1 ppmw. In particular, these advantageous effects are even obtained, when a $C_6$-cut or a $C_6$-$C_8$-cut of FCC gasoline or a $C_6$-cut or a $C_6$-$C_8$-cut of COLO is used as feedstock of the process. In addition, these advantageous effects are obtained even in the case of a very long operation time including start-of-run to end-of-run operating temperature envelope of catalyst, in the case of heavier than expected feedstock being fed to the FCC, RFCC or COLO or in the case of slippage of $C_6$-cyclic olefins and/or $C_7$-isoolefins into the aromatic stream obtained in the solvent based extraction step.

Figure 2:
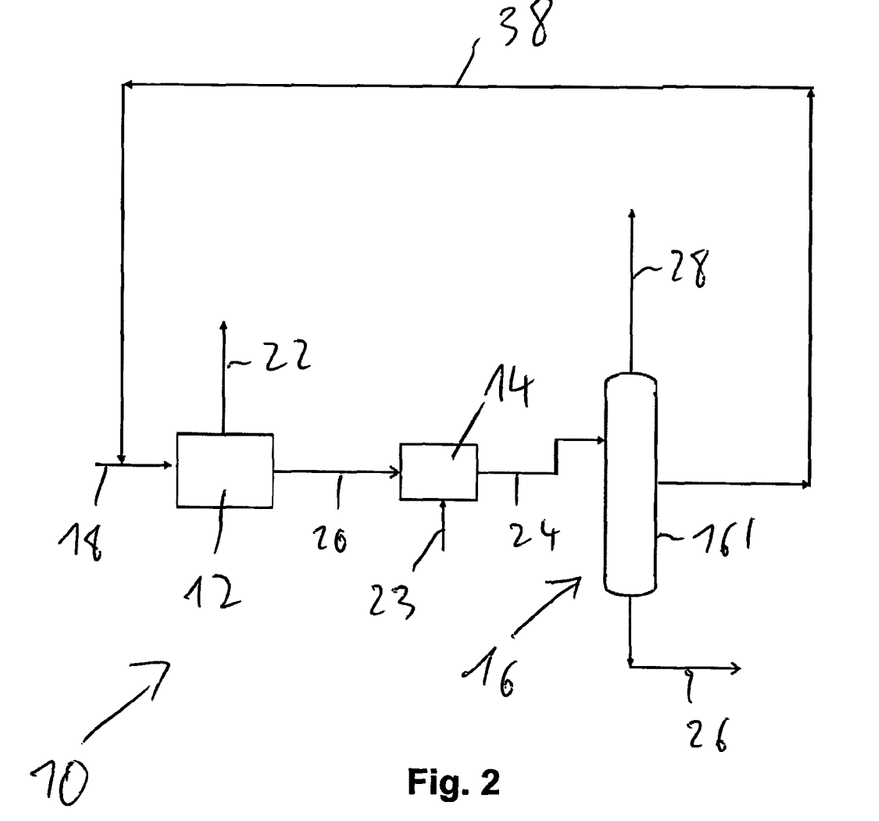
FIG. 2 illustrates a schematic view of a plant for preparing a purified benzene composition from a crude hydrocarbon stream containing benzene in accordance with a first embodiment of the present disclosure.

In the embodiment shown in FIG. 2, the distillation unit 16 comprises one distillation column 16' preferably having 5 to 100 theoretical stages, wherein the distillation is preferably performed at a pressure of 0.1 to 0.2 MPa, such as 0.15 MPa, and at a temperature 90 to 100° C., such as 95° C. This embodiment is particularly suitable when using as feedstock a $C_6$-cut from fluid catalytic cracked naphtha or a coke oven light oil.

Figure 3:
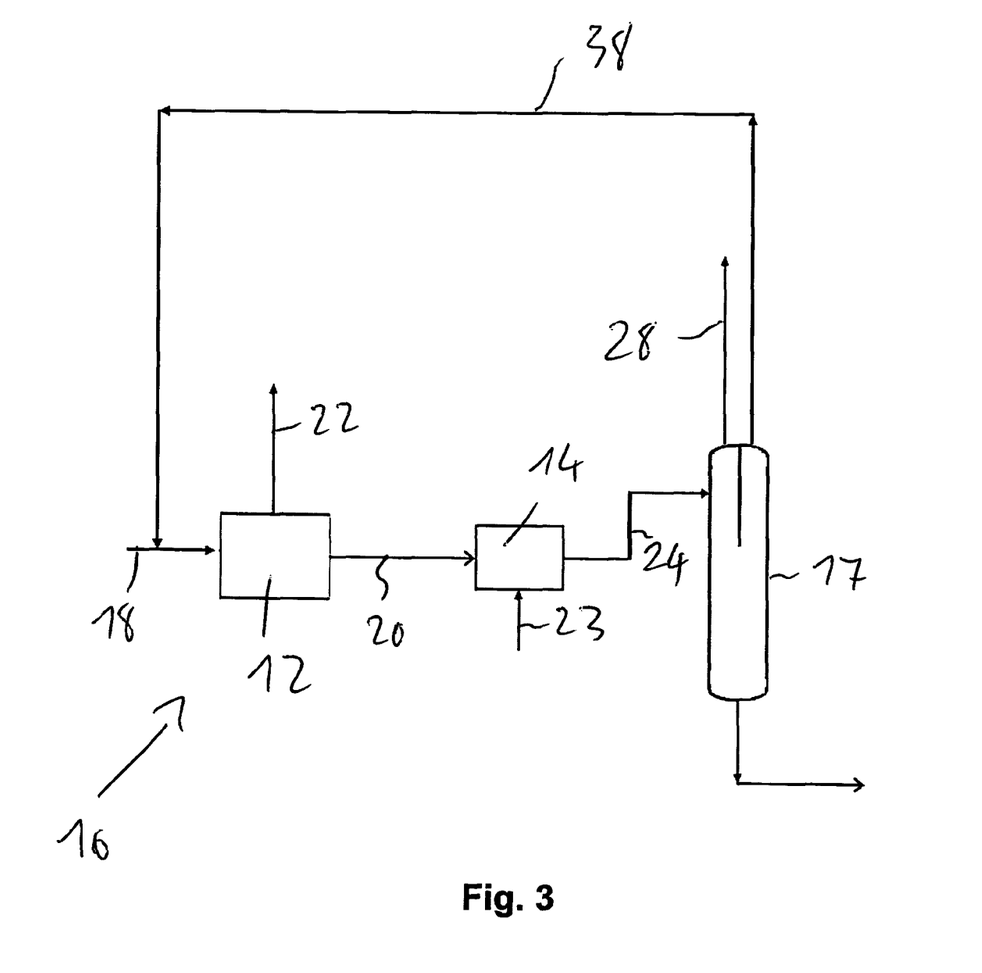
FIG. 3 illustrates a schematic view of a plant for preparing a purified benzene composition from a crude hydrocarbon stream containing benzene in accordance with a second embodiment of the present disclosure.

The embodiment shown in FIG. 3 differs from that shown in FIG. 2 in that the distillation unit 16 comprises a divided wall column 17 and more specifically a top divided wall column 17. Preferably, the wall of the top divided wall column 17 extends from the upper end of the top divided wall column 17 perpendicular downwards over 20 to 70% and preferably over 20 to 50% of the height of the top divided wall column. In this embodiment, at the left side of the overhead of divided wall column 17 an off-gas stream containing low molecular weight hydrocarbons, such as methane, ethane, propane, butane, hydrogen and hydrogen sulfide is obtained, whereas at the right side of the overhead of the divided wall column 17 the further benzene containing stream is obtained and at the bottom of the divided wall column 17 the purified benzene stream is obtained. Preferably, the top divided wall column 17 has 5 to 100 theoretical stages, wherein the distillation is preferably performed at a pressure of 0.1 to 0.2 MPa, such as 0.15 MPa, and at a temperature 90 to 100° C., such as 95° C. The use of the divided wall distillation column 17 has the advantages that the divided wall distillation column 17 requires a reduced height for obtaining the same separation result compared to a distillation column being no divided wall column and that it needs in operation less energy than a traditional distillation column without dividing wall. This embodiment is in particular suitable, when using as a crude hydrocarbon stream a $C_6$-cut from fluid catalytic cracked naphtha or a $C_6$-cut from a coke oven light oil.

The plant shown in FIG. 3 is also in particular suitable, when using as a crude hydrocarbon stream a $C_6$-$C_8$-cut from fluid catalytic cracked naphtha or a $C_6$-$C_8$-cut from a coke oven light oil. In this case, at the bottom of the divided wall distillation column 17 not a purified benzene stream (i.e. not a $C_6$-stream) is obtained, but a purified $C_6$-$C_8$-aromatics stream. This $C_6$-$C_8$-aromatics stream can then be easily processed, for instance in a conventional distillation column, so as to separate the $C_6$-$C_8$-aromatics stream into a purified benzene stream and one or more other aromatics streams.

Figure 4:
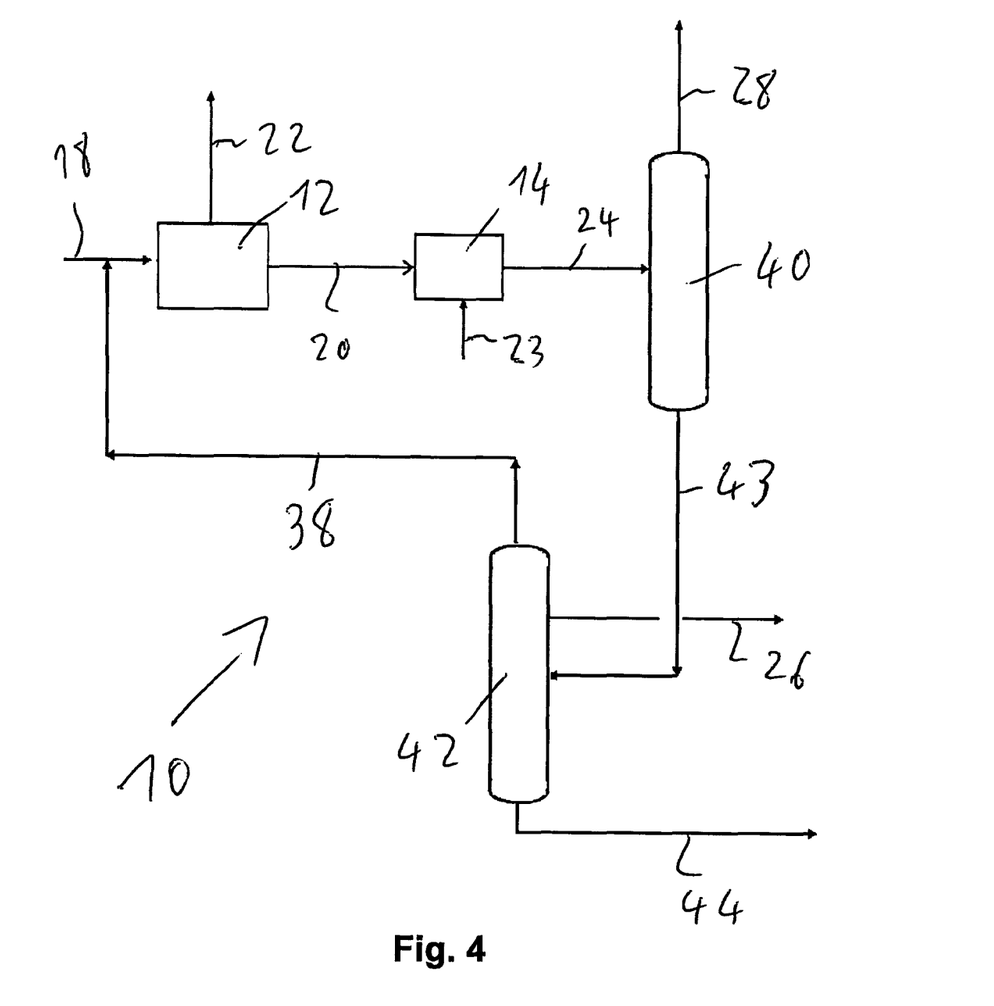
FIG. 4 illustrates a schematic view of a plant for preparing a purified benzene composition from a crude hydrocarbon stream containing benzene in accordance with a third embodiment of the present disclosure.

In the embodiment shown in FIG. 4, the distillation unit 16 comprises two distillation columns 40, 42. The first distillation column 40 preferably has 5 to 30 theoretical stages, whereas the second distillation column 42 has preferably 5 to 100 theoretical stages. While the distillation in the first distillation column 40 is preferably performed at a pressure of 0.1 to 0.2 MPa, such as 0.15 MPa, and at a temperature 90 to 100° C., such as 95° C., the distillation in the second distillation column 42 is preferably performed at a pressure of 0.2 to 0.3 MPa, such as 0.25 MPa, and at a temperature 90 to 140° C. During the distillation performed in the first distillation column 40 at the overhead of the first distillation column an off-gas stream containing low molecular weight hydrocarbons, i.e. $C_1$-$C_4$-hydrocarbons, such as methane, ethane, propane and butane, hydrogen and hydrogen sulfide is obtained and withdrawn via outlet line 28, whereas at the bottom of the first distillation column 40 a liquid with the remaining compounds stream is obtained. This liquid stream is fed via liquid line 43 into the second distillation column 42 and distilled in the second distillation column 42 so as to obtain as side stream of the second distillation column 42 the purified benzene stream, which is withdrawn via outlet line 26, at the overhead of the second distillation column 42 the further benzene containing stream, which is recycled to the solvent based extraction unit 12 via the recirculation line 38, and at the bottom of the second distillation column 42 a $C_{7+}$-stream, which is withdrawn via outlet line 44. This embodiment is in particular suitable, when using as a crude hydrocarbon stream a $C_6$-$C_8$-cut from fluid catalytic cracked naphtha or a coke oven light oil.

Figure 5:
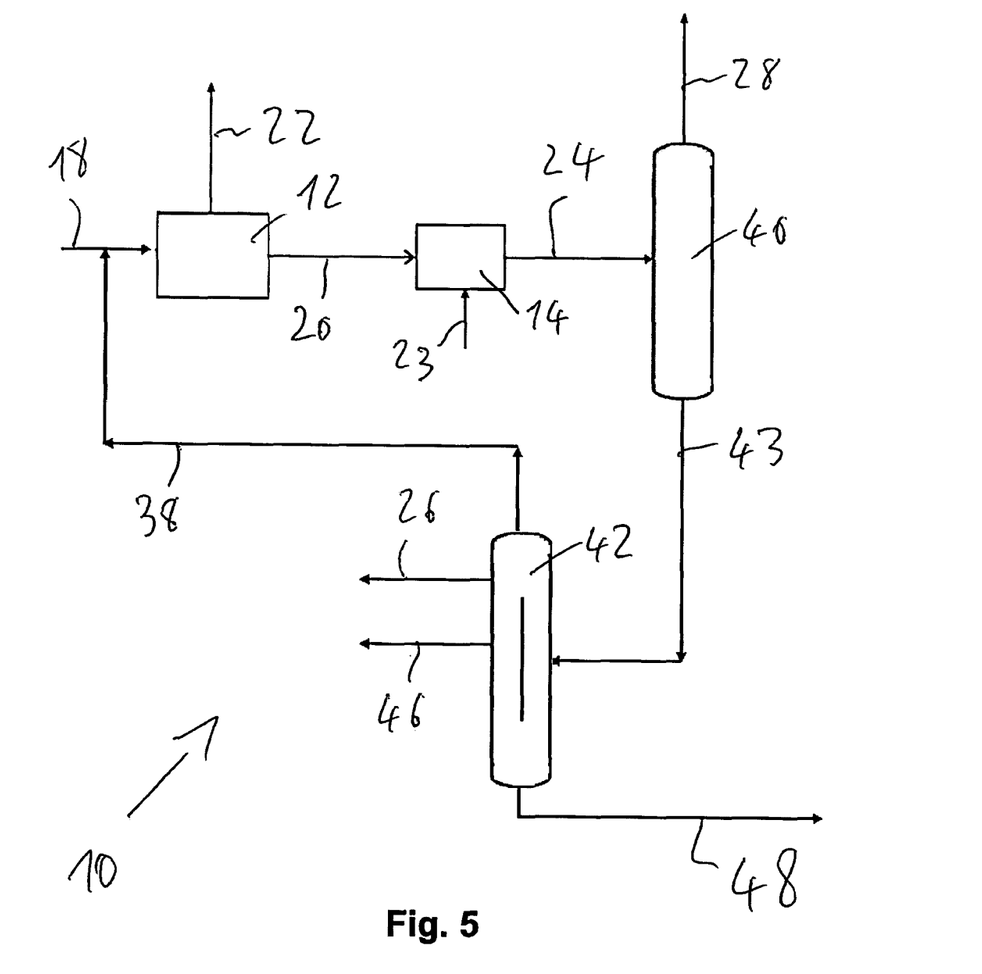
FIG. 5 illustrates a schematic view of a plant for preparing a purified benzene composition from a crude hydrocarbon stream containing benzene in accordance with a fourth embodiment of the present disclosure.

The embodiment shown in FIG. 5 differs from that shown in FIG. 4 in that the distillation unit 16 comprises as second distillation column 42 a divided wall column and more specifically a middle divided wall column. Preferably, the wall of the middle divided wall column 42 extends, seen from the bottom to the overhead of the second distillation column, from a point being located at 10 to 30% of the distance from the bottom to the overhead of the second distillation column to a point being located at 70 to 90% of the distance from the bottom to the overhead of the second distillation column. The first distillation column 40 preferably has 5 to 30 theoretical stages, whereas the second distillation column 42 has preferably 5 to 100 theoretical stages. While the distillation in the first distillation column 40 is preferably performed at a pressure of 0.1 to 0.2 MPa, such as 0.15 MPa, and at a temperature 90 to 100° C. such as 95° C., the distillation in the second distillation column 42 is preferably performed at a pressure of 0.2 to 0.3 MPa, such as 0.25 MPa, and at a temperature 90 to 160° C. During the distillation performed in the first distillation column 40 at the overhead of the first distillation column an off-gas stream containing low molecular weight hydrocarbons. i.e. $C_1$-$C_4$-hydrocarbons, such as methane, ethane, propane and butane, hydrogen and hydrogen sulfide is obtained and withdrawn via outlet line 28, whereas at the bottom of the first distillation column 40 a liquid with the remaining compounds stream is obtained. This liquid stream is fed via liquid line 43 into the second distillation column 42 and is distilled in the second distillation column 42 so as to obtain as a first side stream of the second distillation column 42 the purified benzene stream, which is withdrawn via outlet line 26, as a second side stream of the second distillation column 42 a toluene rich fraction, which is withdrawn via outlet line 46, at the overhead of the second distillation column 42 the further benzene containing stream, which is recycled to the solvent based extraction unit 12 via the recirculation line 38, and at the bottom of the second distillation column 42 a stream rich in mixed xylenes, which is withdrawn via outlet line 48. This embodiment is in particular suitable, when using as a crude hydrocarbon stream a $C_6$-$C_8$-cut from fluid catalytic cracked naphtha or a coke oven light oil.

Subsequently, the present disclosure is described with reference to illustrative, but not limiting examples.

EXAMPLES

Example

With the software ASPEN HYSYS a process has been simulated, which is performed in a plant as shown in FIG. 3 using a $C_6$-cut of fluid catalytic cracked naphtha as crude hydrocarbon stream. A ring loss of 0.4 wt %, which is above the design value of 0.1 wt %, was assumed. Moreover, a benzene recovery of more than 99% has been assumed during the solvent based extraction step and a benzene purity of more than 99.9 wt % has been set as targets.

The composition of the desulfurized aromatic stream, the composition of the further benzene containing stream as well as the temperature conditions, the pressure conditions and other parameters during the distillation in the top divided wall distillation column 17 are shown in the below tables.

Comparative Example

A respective process performed in a plant as shown in FIG. 1 has been simulated using the same $C_6$-cut of fluid catalytic cracked naphtha as crude hydrocarbon stream.

The composition of the desulfurized aromatic stream as well as the temperature conditions, the pressure conditions and other parameters during the distillation in the distillation column 16' are shown in the below tables.

TABLE 1

Composition, temperature and pressure of the desulfurized aromatic stream

| | Comparative Example | Example |
|---|---|---|
| Pressure (bara) | 20.5 | 20.5 |
| Temperature (° C.) | 150 | 150 |
| Compound | kg/h | kg/h |
| Benzene | 9604.2 | 10230.3 |
| Cyclohexane | 45.2 | 48.6 |
| Methylcyclopentane | 0.1 | 0.1 |
| Methane | 0.0 | 0.0 |
| Carbon-Dioxide | 0.0 | 0.0 |
| Ammonia | 0.1 | 0.1 |

TABLE 1-continued

Composition, temperature and pressure of the desulfurized aromatic stream

| | Comparative Example | Example |
|---|---|---|
| Propane | 0.0 | 0.0 |
| Isobutane | 0.2 | 0.2 |
| n-Butane | 4.9 | 4.9 |
| Thiophene | 0.0 | 0.0 |
| Toluene | 3.2 | 3.2 |
| Hydrogen | 1.5 | 1.5 |
| Hydrogen-Sulfide | 2.8 | 2.8 |

It is to be noted that in Example, the feed is higher because it includes the recycled further benzene containing stream.

TABLE 2

Parameters of the distillation column used for the distillation of step c) and product characteristics

| | Comparative Example | Example |
|---|---|---|
| No. of Theoretical stages | 16 | 7 (left side of wall), 7 (right side of wall), 13 non-walled section |
| Column Top Pressure (bara) | 1.5 | 1.5 (left side of wall), 1.5 (right side of wall) |
| Column Bottom Pressure (bara) | 1.66 | 1.7 |
| Column Top Tray Temperature (° C.) | 91.8 | 92.22 (left wall)/ 92.96 (right wall) |
| Column Bottom Tray Temperature (° C.) | 96.85 | 97.9 |
| Overhead Cond Process Side Cooled Temperature (° C.) | 40 | 40 (left condenser)/ 60 (right condenser) |
| Cond Pressure Drop (bara) | 0.5 | 0.5 (left condenser)/ 0.3 (right condenser) |
| Reboiler Duty (Kcal/h) | 20451.3 | 2706005.7 |
| Feed location | $6^{th}$ stage from top | 3 stage on left side of wall |
| Benzene purity (wt %) | 99.49% | 99.80% |
| Column Bottoms Product flow (kg/h) | 9631 | 9616 |

TABLE 3

Composition, temperature and pressure of the further benzene containing stream obtained by the distillation of step c) of the Example.

| Pressure (bara) | 1.2 |
|---|---|
| Temperature (° C.) | 60 |
| Compound | kg/h |
| Benzene | 593.2 |
| Cyclohexane | 32.1 |
| Methylcyclopentane | 0.1 |
| Methane | 0.0 |
| Carbon-Dioxide | 0.0 |
| Ammonia | 0.0 |
| Propane | 0.0 |
| Isobutane | 0.0 |
| n-Butane | 0.0 |
| Thiophene | 0.0 |
| Toluene | 0.0 |
| Hydrogen | 0.0 |
| Hydrogen-Sulfide | 0.00 |

The invention claimed is:

1. A process for preparing a purified benzene composition from a crude hydrocarbon stream containing at least 10% by volume of benzene comprising the following steps:

a) subjecting the crude hydrocarbon stream and a further recycled benzene containing stream to a solvent based extraction so as to produce a benzene enriched aromatic stream and a benzene depleted non-aromatic stream,
b) subjecting the benzene enriched aromatic stream to a hydrodesulfurization so as to obtain a desulfurized aromatic stream,
c) subjecting the desulfurized aromatic stream to a distillation so as to produce a purified benzene stream and a further benzene containing stream, wherein the further benzene containing stream comprises benzene and at least one of cyclohexane, methylcyclopentane, 2,3 dimethyl pentane and 2,4 dimethyl pentane and has a benzene concentration of between less than 100% by weight and the azeotropic benzene concentration in the azeotrope formed of these compounds as dictated by the vapor-liquid equilibrium of the compounds contained in the further benzene containing stream, and
d) at least partially recycling the further benzene containing stream.

2. The process in accordance with claim 1, wherein the crude hydrocarbon stream contains, based on 100% by weight, at least 20% by volume of benzene.

3. The process in accordance with claim 1, wherein the crude hydrocarbon stream contains, based on 100% by weight, i) 20 to 60% by volume of paraffins, ii) 10 to 50% by volume of olefins and iii) 5 to 40% by volume of naphthenes.

4. The process in accordance with claim 1, wherein the crude hydrocarbon stream is a $C_6$-cut or a $C_6$-$C_8$-cut from fluid catalytic cracked naphtha or a $C_6$-cut or a $C_6$-$C_8$-cut from a coke oven light oil.

5. The process in accordance with claim 1, wherein the crude hydrocarbon stream is mixed with the recycled further benzene containing stream to obtain a feed stream, which is subjected to the solvent based extraction.

6. The process in accordance with claim 1, wherein the crude hydrocarbon stream and the recycled further benzene containing stream are separately fed to the solvent based extraction.

7. The process in accordance with claim 1, wherein the crude hydrocarbon stream and the recycled further benzene containing stream are subjected to an extractive distillation.

8. The process in accordance with claim 1, wherein the solvent used in the solvent based extraction is selected from a group consisting of sulfolane, 3-methylsulfolane, 2,4-dimethylsulfolane, 3-ethylsulfolane, N-methyl pyrrolidone, 2-pyrrolidone, N-ethyl pyrrolidone, N-propyl pyrrolidone, N-formyl morpholine, dimethylsulfone, diethylsulfone, methylethylsulfone, dipropylsulfone, dibutylsulfone, tetraethylene glycol, triethylene glycol, dimethylene glycol, ethylene glycol, ethylene carbonate, and propylene carbonate or a combination thereof.

9. The process in accordance with claim 1, wherein the desulfurized aromatic stream is subjected to one or more distillation steps, wherein at least one distillation step is performed with a top divided wall column, wherein one distillation step is performed and the wall of the top divided wall column extends from the upper end of the top divided wall column perpendicular downwards over 20 to 70% of the height of the top divided wall column.

10. The process in accordance with claim 1, wherein the desulfurized aromatic stream is subjected to two distillation steps, wherein the desulfurized aromatic stream is subjected to a first distillation step in a first distillation column so as to obtain at the overhead of the first distillation column an off-gas stream containing $C_1$-$C_7$-hydrocarbons, hydrogen and hydrogen sulfide and at the bottom of the first distillation column a liquid stream with the remaining compounds, wherein the liquid stream is subjected to a second distillation step in a second distillation column so as to obtain as side stream of the second distillation column the purified benzene stream, at the overhead of the second distillation column the further benzene containing stream and at the bottom of the second distillation column a $C_{7+}$-stream.

11. The process in accordance with claim 1, wherein the desulfurized aromatic stream is subjected to two distillation steps, wherein the desulfurized aromatic stream is subjected to a first distillation step in a first column so as to obtain at the overhead of the first distillation column an off-gas stream containing $C_1$-$C_7$-hydrocarbons, hydrogen and hydrogen sulfide and at the bottom of the first distillation column a liquid stream with the remaining compounds, wherein the liquid stream is subjected to a second distillation step in a second middle divided wall column so as to obtain as first side stream the purified benzene stream, as second side stream a toluene rich stream, at the overhead of the second distillation column the further benzene containing stream and at the bottom of the second distillation column a stream enriched in xylenes.

* * * * *